United States Patent
Thelu et al.

(10) Patent No.: US 12,178,412 B2
(45) Date of Patent: Dec. 31, 2024

(54) DEVICE FOR COLLECTING INTESTINAL FLUID

(71) Applicants: UNIVERSITE GRENOBLE ALPES, Saint Martin d'Heres (FR); CENTRE NATIONAL DE LA RECHERCHE SCIENTIFIQUE, Paris (FR); CENTRE HOSPITALIER UNIVERSITAIRE GRENOBLE ALPES, La Tronche (FR)

(72) Inventors: Jacques Thelu, Crolles (FR); Philippe Cinquin, Saint Nazaire les Eymes (FR); Donald Keith Martin, Gieres (FR); Thomas Soranzo, Grenoble (FR); Jean-Pierre Alcaraz, Pontcharra (FR); Jean-Marc Kweter, Mont de Marsan (FR)

(73) Assignees: UNIVERSITE GRENOBLE ALPES, Saint Martin d'Heres (FR); CENTRE NATIONAL DE LA RECHERCHE SCIENTIFIQUE, Paris (FR); CENTRE HOSPITALIER UNIVERSITAIRE GRENOBLE ALPES, La Tronche (FR)

( * ) Notice: Subject to any disclaimer, the term of this patent is extended or adjusted under 35 U.S.C. 154(b) by 925 days.

(21) Appl. No.: 16/759,286

(22) PCT Filed: Oct. 24, 2018

(86) PCT No.: PCT/EP2018/079077
§ 371 (c)(1),
(2) Date: Apr. 24, 2020

(87) PCT Pub. No.: WO2019/081539
PCT Pub. Date: May 2, 2019

(65) Prior Publication Data
US 2020/0297329 A1    Sep. 24, 2020

(30) Foreign Application Priority Data

Oct. 25, 2017    (FR) ...................................... 1760069

(51) Int. Cl.
*A61B 10/00*    (2006.01)

(52) U.S. Cl.
CPC ..................... *A61B 10/0045* (2013.01); *A61B 2010/0061* (2013.01)

(58) Field of Classification Search
CPC .................... A61B 10/0045; A61B 2010/0061
(Continued)

(56) References Cited

U.S. PATENT DOCUMENTS

| | | | |
|---|---|---|---|
| 3,688,763 | A | 9/1972 | Cromarty |
| 5,971,942 | A | 10/1999 | Gu et al. |

(Continued)

FOREIGN PATENT DOCUMENTS

| | | |
|---|---|---|
| CN | 104203117 A | 12/2014 |
| CN | 106821423 A | 6/2017 |

(Continued)

OTHER PUBLICATIONS

International Search Report issued in corresponding International Application No. PCT/EP2018/079077, mailed Jan. 30, 2019, pp. 1-2, European Patent Office, Rijswijk, Netherlands.

(Continued)

*Primary Examiner* — Eric J Messersmith
*Assistant Examiner* — Chanel J Jhin
(74) *Attorney, Agent, or Firm* — HAUPTMAN HAM, LLP

(57) ABSTRACT

The application relates to a device for collecting a sample of intestinal fluid comprising a polymeric inner material having an at least partially compressed open cell structure, having a volume $V_i$ and being suitable for swelling to a volume greater than or equal to $1.1 \times V_i$ by absorbing intestinal fluid, said material being encased with an elastic polymeric casing impervious to digestive fluid, said casing comprising at least one opening allowing the intake of intestinal fluid into the inner material, a gastro-resistant material suitable for dissolving in intestinal fluid at 37° C. being disposed on top of each opening, and at least one mechanism for closing the opening(s).

11 Claims, 3 Drawing Sheets

(58) Field of Classification Search
USPC .......................................................... 600/582
See application file for complete search history.

(56) References Cited

U.S. PATENT DOCUMENTS

| | | |
|---|---|---|
| 2007/0173738 A1 | 7/2007 | Stoltz |
| 2015/0119756 A1 | 4/2015 | Husmark et al. |
| 2020/0138416 A1* | 5/2020 | Shalon ............... A61B 10/0045 |

FOREIGN PATENT DOCUMENTS

| | | |
|---|---|---|
| DE | 19801573 A1 | 7/1999 |
| EP | 1530950 A1 | 5/2005 |
| GB | 2554444 A | 4/2018 |
| WO | 2018060673 A1 | 4/2018 |

OTHER PUBLICATIONS

Written Opinion issued in corresponding International Application No. PCT/EP2018/079077, mailed Jan. 30, 2019, pp. 1-6, European Patent Office, Rijswijk, Netherlands.

* cited by examiner

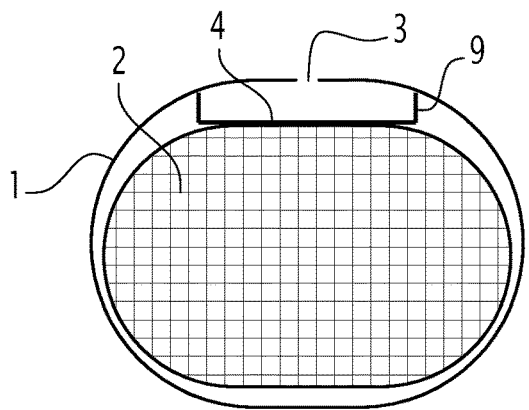
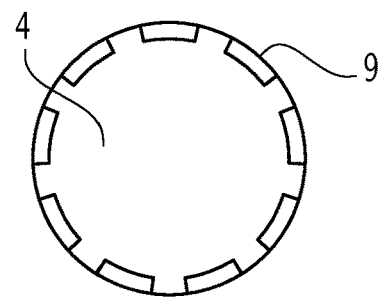
FIG.5  FIG.5A
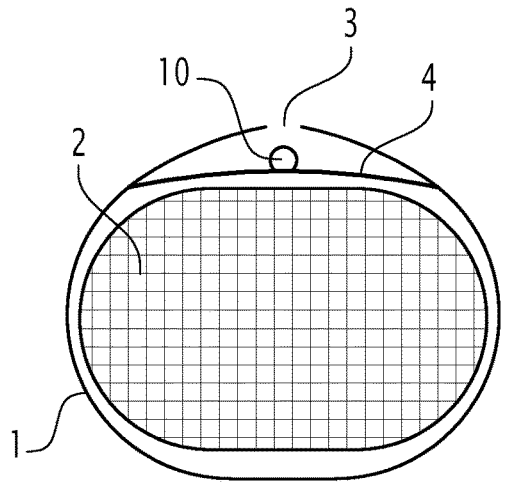
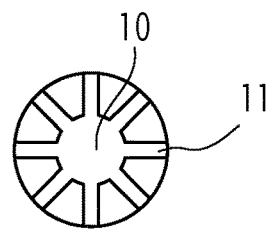
FIG.6  FIG.6A
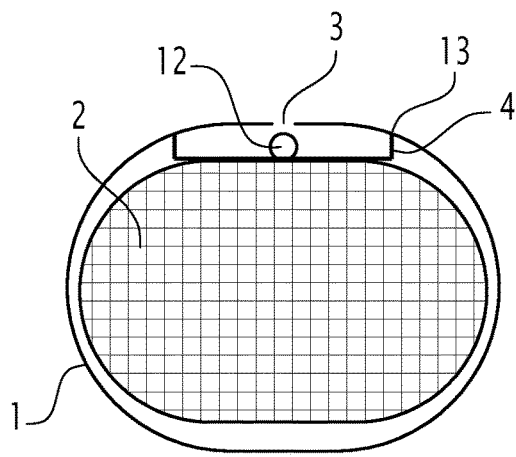
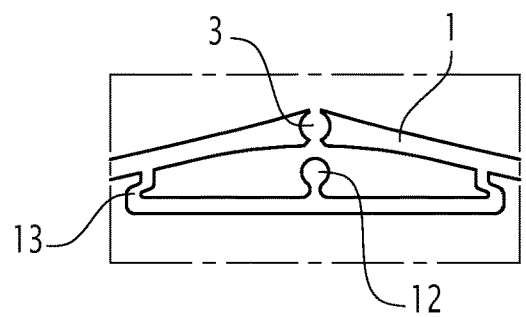
FIG.7  FIG.7A

DEVICE FOR COLLECTING INTESTINAL FLUID

RELATED APPLICATIONS

This application is a U.S. National Stage of International Application No. PCT/EP2018/079077, filed on Oct. 24, 2018, which claims the priority and benefit of French Application No. 1760069, filed on Oct. 25, 2017.

FIELD OF THE INVENTION

The present invention relates to a device for collecting a sample of intestinal fluid, from humans or animals, particular for research and diagnostic purposes.

TECHNOLOGICAL BACKGROUND

Knowledge of the digestive system and the microbiota thereof is considered as a subject of major interest in human or animal health. In terms of disease diagnostics, it is essential to be able to characterise, qualitatively and quantitatively, the microbiota contained in different locations of the digestive system, in particular in the intestines.

At the present time, the majority of analyses are performed on stools, therefore restricting microbiota observation possibilities. While current analytical methods are constantly improved and less expensive, there is a need for an autonomous means, with no negative effect on health, that is simple and expensive, for sampling the microbiota from intestinal fluid.

Devices for collecting intestinal fluid are known, particularly from the applications DE 198 01 573 and U.S. Pat. No. 5,971,942 which describe capsules for taking samples formed of a casing delimiting an internal volume wherein a low internal pressure prevails, the intestinal liquid being then aspirated into the capsule via an opening by the pressure differential, and the closure of the capsule being obtained by equilibrium of the pressures outside and inside the capsule.

The device according to U.S. Pat. No. 5,971,942 is characterised by a small internal volume and a low internal pressure. The device according to DE 198 01 573 comprises a mechanism for closing an opening comprising a foam which is not in the compressed state.

Thus, the aim of the present invention is that providing a device for collecting a sample of intestinal fluid at different levels in the intestines.

A further aim of the present invention is that of providing such a device which makes it possible to collect variable volumes, while remaining easy to swallow for the patient.

A further aim of the present invention is that of providing such a device which is inexpensive and readily usable and retrievable.

Further aims of the present invention will emerge on reading the following description.

SUMMARY

For this purpose, the present invention relates to a device for collecting a sample of intestinal fluid comprising:
  a polymeric inner material:
    having an at least partially compressed open cell structure, and
    having a volume $V_i$,
  an elastic polymeric casing impervious to digestive fluid, said casing comprising at least one opening,
    a gastro-resistant material suitable for dissolving in intestinal fluid at 37° C. being disposed on top of each opening; and
    at least one mechanism for closing the opening(s).

The intake of intestinal fluid into the device causes swelling of the inner material which induces the closure of the mechanism for closing the opening(s).

The inner material is suitable for swelling to a volume greater than or equal to $1.1 \times V_i$ by absorbing intestinal fluid.

The casing encases the inner material, said at least one opening allowing the intake of intestinal fluid into the inner material.

Thus, swelling of the inner material causes elastic deformation of the casing.

The invention thus enables precise (pre)determination of the volume of intestinal liquid (to be collected) collected, in that the swelling force of the inner material is equilibrated with the force applied by the casing due to the elastic deformation thereof.

The term "intestinal fluid" denotes the fluid present in the intestines, this fluid comprising a very large number of live micro-organisms, otherwise known as the "microbiota". The term "digestive fluid" denotes gastric or intestinal fluid.

Hereinafter, the expression "between X and Y" means that the limits X and Y are included. The term "polymeric" denotes comprising a polymer.

Preferably, the polymeric inner material comprised in the device has a solubility in intestinal fluid measured at 37° C. less than or equal to 1% by mass. Preferably, the inner material is insoluble in intestinal fluid at 37° C. The term "insoluble" denotes that the inner material does not dissolve (solubility of 0% by mass) after submerging in intestinal fluid at 37° C. throughout the digestive process, preferably for at least 24 hours.

Advantageously, the polymer of the inner material is chosen from among at least partially cross-linked polyvinyl alcohols, at least partially cross-linked poly(meth)acrylic acids and salts thereof, at least partially cross-linked polysaccharides, or a mixture thereof. Among the polysaccharides, mention may be made of dextran or one of the derivatives thereof.

The at least partial cross-linking of these polymers ensures that the solubility thereof at 37° C. in intestinal fluid is less than or equal to 1% by mass, preferably 0% (insoluble). Indeed, the non-cross-linked polymers mentioned above are generally soluble in water, and therefore in intestinal fluid at 37° C.

The polymeric inner material has an open cell structure and a volume $V_i$ which corresponds to the volume thereof before ingestion. Therefore, it is presented in the form of a foam or a sponge.

The open cell structure of the inner material comprises cells separated from one another by polymeric walls, the mean thickness of said walls being preferably between 2 μm and 500 μm. The mean thickness of the cell walls is measured by scanning electron microscopy.

The cells of the open cell structure are generally at least partially, or completely, filled with gas, preferably air. They may comprise water.

The open cell structure is at least partially compressed, whereby the inner material is suitable for swelling by absorbing intestinal fluid, to a volume greater than or equal to $1.1 \times V_i$, particularly greater than or equal to $2 \times V_i$, preferably greater than or equal to $6 \times V_i$.

The term "elastic casing" denotes that the casing has an elasticity such that it enables swelling of the inner volume to a volume greater than or equal to $1.1 \times V_i$, preferably to a volume of $2 \times V_i$ to $6 \times V_i$. Typically, the polymeric casing is stretchable at 25° C. under a force of 1N over a length between 2 times and 6 times the initial length thereof. Preferably, the elastic casing has a hardness between 30 and 55 Shore (shore A standardised method). Preferably, the polymer of the casing has a Young modulus between 1.1 and 1.9 MPa.

Preferably, the polymer of the casing is chosen from among latexes, polyvinyls, nitrile polymers, silicone, and a mixture thereof, preferably the polymer of the casing is chosen from among nitrile polymers such as a butadiene-acrylonitrile copolymer.

As the casing encases the inner material, the swelling of the inner material once ingested is limited by the elasticity of the casing. Preferably, before ingestion, the casing is in the unstretched state.

The term "casing impervious to gastric fluid" denotes that, at 37° C., except at the level of the opening(s), digestive fluid does not pass through the casing. The casing is therefore impervious to digestive fluid. Generally, the casing has pores of mean diameter as measured by scanning electron microscopy of less than 0.2 µm. Preferably, the casing is free from pores.

Preferably, the casing is stable in relation to digestive fluid. The term "stable" denotes that the casing does not disintegrate, the chemical composition thereof and the tightness thereof are not modified in contact with digestive fluid throughout the digestive process, preferably for at least 24 hours.

The casing defines an inner space, wherein the inner material is disposed. The inner material generally occupies at least 80%, particularly at least 90%, preferably at least 95% of the volume of the inner space formed by the casing. Preferably, the difference between the pressure inside the casing (and therefore inside the inner material encased therein) and atmospheric pressure is less than 5%, particularly less than 1%, preferably 0%. Generally, the pressure inside the casing (and therefore inside the inner material encased therein) is atmospheric pressure (1 bar).

Preferably, the casing comprises 1, 2, 3, 4 or 5 openings, preferably a single opening. The opening allows the intake of intestinal fluid into the device, and therefore into the inner material.

The casing may comprise a metal wire for reinforcing the casing so that it withstands peristaltic movements better. This metal wire may be disposed in the thickness of the casing. Preferably, it is a ferromagnetic metal wire.

Coloured markers may be integrated on the surface of the casing to allow recognition of retrieved devices. A silicon chip, an RFID chip or equivalent may also be used.

The term "gastro-resistant material" denotes a material that does not disintegrate and does not dissolve in contact with gastric fluid. The term "suitable for dissolving in intestinal fluid at 37° C." denotes that the limit of solubility of the gastro-resistant material is greater than 95% by mass, preferably greater than 98% by mass in intestinal fluid at 37° C.

Preferably, the gastro-resistant material is suitable for dissolving in intestinal fluid at a given pH. Indeed, the solubility of the gastro-resistant material may essentially be dependent on the pH of the medium wherein it is located. Thus, preferably, the gastro-resistant material is insoluble at 37° C. in the presence of an acidic pH (less than 7), preferably, it is insoluble at 37° C. at a pH less than 5. The term "insoluble" denotes the limit of solubility of the gastro-resistant material at a pH less than 5 is less than or equal to 1% by mass, preferably equal to 0% by mass. The pH of the intestinal fluid varies from 5 to 8 according to the exact location of the intestine where it is located. It is known to those skilled in the art that the fasting stomach is characterised by a pH between 1.5 and 3, this pH being between 2 and 5 after a meal and progressively neutralised on leaving the stomach. Thus, the pH at the level of the duodenum is between 5.4 and 6.1, the pH at the level of the ileum is between 7 and 8, the caecum and the colon have a pH between 5.5 and 7, and finally the rectum has a pH equal to 7. Thus, those skilled in the art will readily understand that the gastro-resistant material is chosen according to the solubility thereof at the pH at the location where the intestinal fluid is to be collected. Preferably, a gastro-resistant material suitable for dissolving in intestinal fluid at 37° C. is disposed on top of the entire device. For example, a gastro-resistant hard capsule suitable for dissolving in intestinal fluid at 37° C. can cover the assembly formed by the casing and the inner material. The gastro-resistant material is suitable for dissolving completely in intestinal fluid at 37° C. when the pH reaches a determined value. Preferably, the gastro-resistant material dissolves rapidly, in a time of less than 10 min, preferably less than 5 min.

Preferably, the gastro-resistant material is chosen from among poly(methyl methacrylate), cellulose acetophthalate, carboxymethylcellulose, hypromellose aceto-succinate, polyvinyl acetate phthalate, shellacs, etc. Advantageously, the gastro-resistant material is chosen from among the compounds Eudragit® L30 D-55 and Eudragit® L100-55 marketed by the company Evonik©

Advantageously, one or more intermediate layer(s), typically an alginate layer, may be disposed between the opening and the gastro-resistant material. Preferably, no intermediate layer is present between the opening and the gastro-resistant material.

In an embodiment, the casing and the inner material are encased in an alginate hard capsule, said hard capsule being coated with gastro-resistant material such as those mentioned above. The alginate hard capsule is completely soluble at 37° C. in intestinal fluid, preferably the limit of solubility of the alginate hard capsule in intestinal fluid at 37° C. is greater than 95% by mass. The exterior of the hard capsule is rendered gastro-resistant, particularly thanks to film-coating with a gastro-resistant material.

Advantageously, the device may be in cylindrical, spherical or ellipsoid form, preferably cylindrical. Preferably, the device may be a flat cylinder, in half-moon form.

Preferably, the device is suitable for collecting a volume of intestinal fluid between 0.01 mL and 1 mL, preferably a volume of intestinal fluid equal to 0.3 mL.

The mechanism for closing the opening(s) makes it possible to close each opening of the casing by blocking same. The device may comprise as many mechanisms for closing openings as there are openings. Alternatively, a single closing mechanism may make it possible to close several openings.

The different closing mechanisms below are described for closing a single opening but may be used for closing several thereof. In the case where the casing comprises several openings, identical or different closing mechanisms may be used.

BRIEF INTRODUCTION OF THE DRAWINGS

Different mechanisms for closing the opening(s) of the device will now be described in more detail using embodiments taken as non-limiting examples with reference to the appended figures wherein:

FIG. 5 represents a fourth embodiment of the closing mechanism, said mechanism comprising a flap comprising contacts;

FIG. 5A represents a top view of the closing mechanism represented in FIG. 5;

FIG. 6 represents a fifth embodiment of the closing mechanism, said mechanism comprising a flap comprising a press stud;

FIG. 6A represents a top view of the closing mechanism represented in FIG. 6;

FIG. 7 represents a sixth embodiment of the closing mechanism, said mechanism comprising a flap, said flap comprising a press stud and being connected to the casing;

FIG. 7A represents an enlargement of the closing mechanism represented in FIG. 7;

DETAILED DESCRIPTION

Preferably, the closing mechanisms according to embodiments 1 to 7 and 9 comprise a flap 4. This flap is generally impervious to intestinal fluid. The term "flap impervious to intestinal fluid" denotes that, at 37° C., intestinal fluid does not pass through the flap. Preferably, the flap is made of polyethylene or silicone. The flap may be in disk form which, once the closing mechanism is closed, completely blocks the opening 3.

Preferably, the flap is a disk having a thickness between 0.1 mm and 0.4 mm. Preferably, the surface area of the flap is greater than the surface area of the opening.

Figure 1:
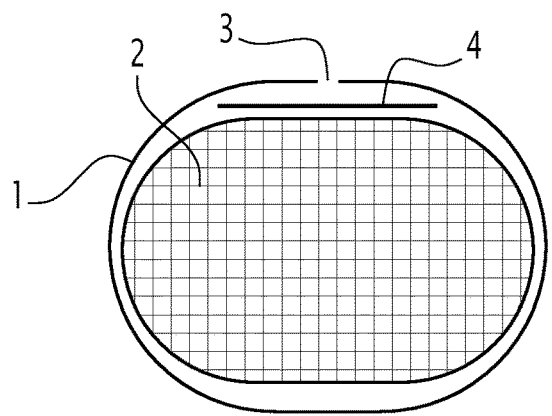
FIG. 1 represents a first embodiment of the closing mechanism, said mechanism comprising a flap.

According to a first embodiment illustrated by FIG. 1, the mechanism for closing the opening 3 comprises a flap 4 impervious to intestinal fluid, the flap being inserted between the casing 1 and the inner material 2 and disposed under the opening 3.

According to a second embodiment, the mechanism for closing the opening 3 of the collection device may comprise:

a flap 4 impervious to intestinal fluid, the flap being inserted between the casing 1 and the inner material 2 and disposed under the orifice 3;

a film 5 or particles 6 of mean diameter between 0.10 mm and 2 mm, said film 5 or said particles 6 comprising a polymer suitable for dissolving at 37° C. in intestinal fluid, said film 5 or said particles 6 being disposed between the flap 4 and the casing 1, where the film 5 or the particles 6 and the casing 1 form together channels whereby intestinal fluid is suitable for circulating and attaining the inner material 2.

Figure 2:
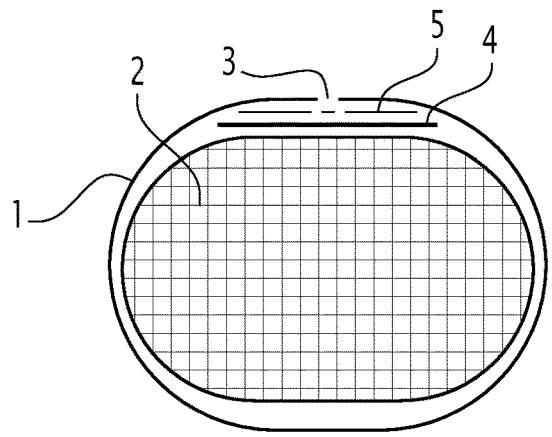
FIG. 2 represents a first alternative of the second embodiment of the closing mechanism, said mechanism comprising a flap and a polymeric film.

More particularly, according to a first alternative of the second embodiment represented in FIG. 2, the mechanism for closing the opening 3 of the device comprises:

a flap 4 impervious to intestinal fluid, the flap being inserted between the casing 1 and the inner material 2 and disposed under the orifice 3;

a film 5 comprising a polymer suitable for dissolving at 37° C. in intestinal fluid, the film being disposed between the flap 4 and the casing 1, where the film 5 and the casing 1 form together channels whereby intestinal fluid is suitable for circulating and attaining the inner material.

The polymer of the film 5 is suitable for dissolving in intestinal fluid at 37° C. in a time of less than 5 minutes.

Preferably, the polymer of the film 5 is biocompatible. Preferably, the polymer of the film 5 suitable for dissolving in intestinal fluid at 37° C. is a polymer carrying hydroxyl, carboxylic acid or carboxylate functions, preferably the polymer of the film 5 is made of polyvinyl alcohol (PVA). Preferably, the film 5 has an embossed structure.

Figure 3:
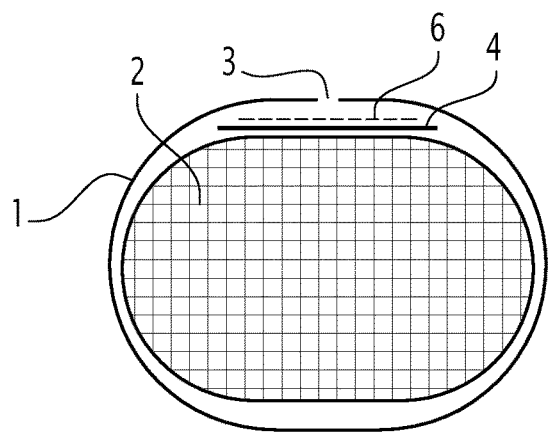
FIG. 3 represents a second alternative of the second embodiment of the closing mechanism, said mechanism comprising a flap, and polymer particles.

According to a second alternative of the second embodiment represented in FIG. 3, the mechanism for closing the opening of the collecting device comprises:

a flap 4 impervious to intestinal fluid, the flap being inserted between the casing 1 and the inner material 2 and disposed under the orifice;

particles 6 of mean diameter between 0.10 mm and 2 mm disposed between the flap 4 and the casing 1, and comprising a polymer suitable for dissolving at 37° C. in intestinal fluid;

where the particle 6 and the casing 1 form together channels whereby intestinal fluid is suitable for circulating and attaining the inner material.

The mean diameter of the particles 6 may be determined by scanning electron microscopy. Preferably, the polymer comprised in the particles 6 is suitable for dissolving in intestinal fluid in a time of less than 5 minutes. Preferably, the polymer comprised in the particles is biocompatible. Preferably, this polymer of the particles 6 is a polyethylene glycol (PEG), typically a polyethylene glycol of molecular mass less than 20,000 g/mol, preferably of molecular mass equal to 8000 g/mol. PEGs of higher molecular masses take more time to dissolve in intestinal fluid and are less suitable for the present invention.

Figure 4:
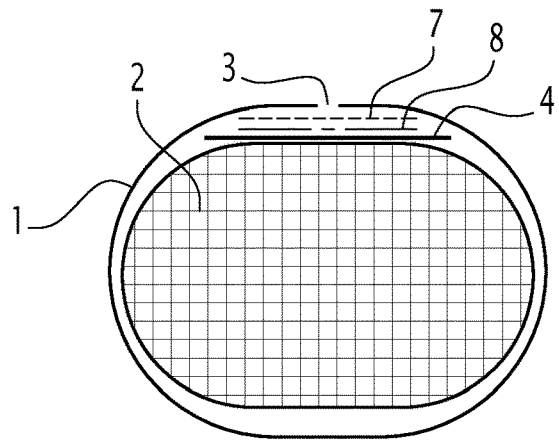
FIG. 4 represents a third embodiment of the closing mechanism, said mechanism comprising, a flap, and two polymers in powder or film form.

According to a third embodiment represented in FIG. 4, the mechanism for closing the opening 3 comprises:

a flap 4 impervious to intestinal fluid, the flap being inserted between the casing 1 and the inner material 2 and disposed under the orifice 3;

a film or particles 7 disposed between the flap 4 and the casing 1 and comprising a first polymer carrying hydroxyl, carboxylic acid and/or carboxylate functions; and a film or particles 8 disposed between the film or the particles 7 and the flap 4 and comprising a second polymer carrying hydroxyl, carboxylic acid and/or carboxylate functions;

where the film or the particles 7 comprising the first polymer, the film or the particles 8 comprising the second polymer and the casing 1 form together channels whereby intestinal fluid is suitable for circulating and attaining the inner material 2, on condition that:

when the first polymer carries hydroxyl functions, the second polymer carries carboxylic acid and/or carboxylate functions, when the first polymer carries carboxylic acid and/or carboxylate functions, the second polymer carries hydroxyl functions, the first and second polymers are suitable for reacting together to form a polyester during the circulation of intestinal liquid in the channels.

Indifferently, the first and second polymers may be in the form of film or particles 7, 8. The mean particle diameter may be between 0.10 mm and 2 mm, and be measured by scanning electron microscopy. The thickness of the polymer film 7, 8 may be between 0.1 mm and 0.5 mm.

In this embodiment, the first and second polymers are suitable for forming a polyester which blocks the channels whereby the intestinal fluid circulates, and which also blocks the opening. The polyester formed does not dissolve in intestinal fluid at 37° C., preferably the limit of solubility thereof at 37° C. in intestinal fluid is less than or equal to 1% by mass, preferably 0% by mass. Preferably, the first and second polymers are biocompatible and in the dehydrated state. Preferably, these polymers carrying hydroxyl, carboxylic acid and/or carboxylate functions are hydrophilic and fully soluble in intestinal fluid, i.e. the limit of solubility thereof in intestinal fluid at 37° C. is greater than 95% by mass.

Preferably, the polymer carrying hydroxyl functions is polyvinyl alcohol. Advantageously, the polymer carrying carboxylic acid and/or carboxylate functions is chosen from among polyacrylic acid or one of the salts thereof, preferably it is sodium polyacrylate.

According to a fourth embodiment represented in FIG. 5, the flap 4 is moulded, has a circular shape and includes on the circumference thereof intercalation structures 9 also suitable for being moulded. These intercalation structures represent types of contacts and form a single piece with the flap 4. Preferably, the flap 4 (including the intercalation structures 9 thereof) comprises the same polymer as that of the casing 1, which enables good adhesion between the flap 4 and the casing 1 when the closing mechanism is closed. For example, the polymer of the flap 4 and of the casing 1 is a silicone. Typically, the flap is moulded in silicone of hardness of 30 shore T which gives same both flexibility and controlled rigidity as well as very good adhesion to a silicone casing.

According to a fifth embodiment represented in FIGS. 6 and 6A, the flap 4 includes at the centre thereof an excrescence in the form of a press stud 10, suitable for being polymeric. The top part of the press stud is structured in the form of radiant channels 11.

According to a sixth embodiment represented in FIG. 7, the flap 4 includes at the centre thereof a press stud 12 having at the periphery point links 13 with the casing 1. The flap 4 (including the press stud 12 and the point links 13 thereof) comprises the same polymer as that of the casing 1, which enables good adhesion between the flap 4 and the casing 1 when the closing mechanism is closed. For example, the polymer of the flap 4 and of the casing 1 is a silicone. The flap 4 and link 13 assembly may be moulded in a one-piece fashion with the casing 1 such that it cannot move laterally. The links 13 ensure that the press stud 12 is consistently centred facing the opening 3. The part may be for example moulded in silicone of hardness of 30 shore T which gives same both flexibility and controlled rigidity as well as very good adhesion to a silicone casing.

Figure 8:
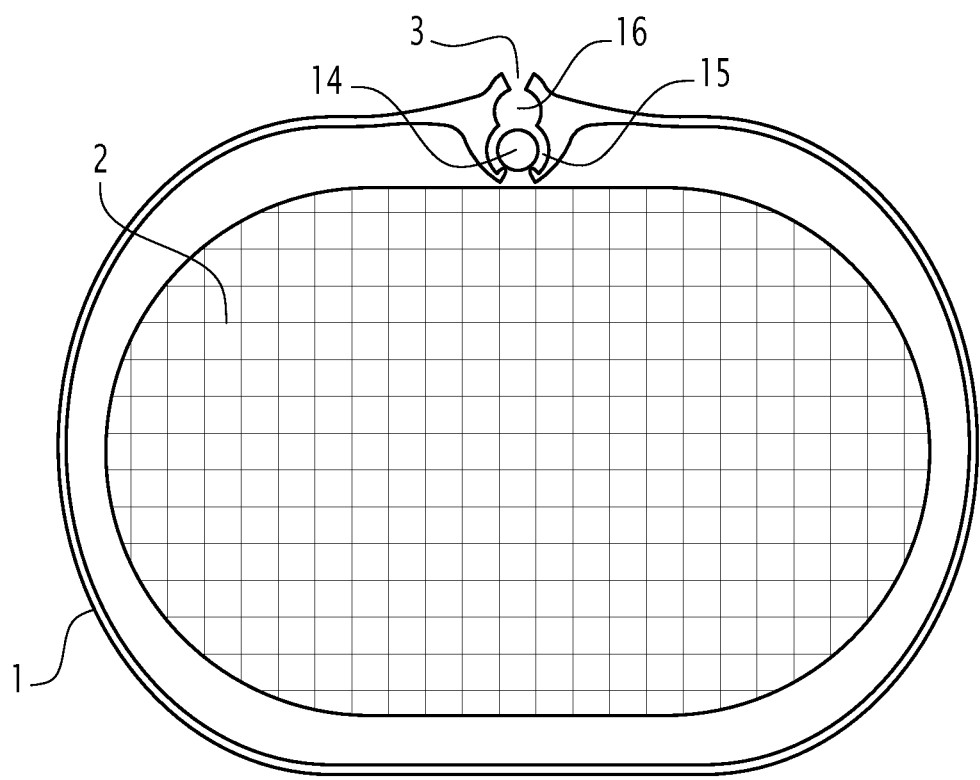
FIG. 8 represents a seventh embodiment of the closing mechanism comprising an obturator.

According to a seventh embodiment represented in FIG. 8, the opening 3 is such that it can receive a small bead 14, for example made of glass or of polystyrene, having typically a diameter of about 1 mm, the whole acting as an obturator. This obturator consists of two lower 15 and upper 16 chambers suitable for receiving the bead 14, the lower chamber 15 being wider than the upper chamber 16. When the bead is located in the lower chamber 15, the opening is open. When the bead is located in the upper chamber 16, the opening is closed.

Figures 9, 9A:
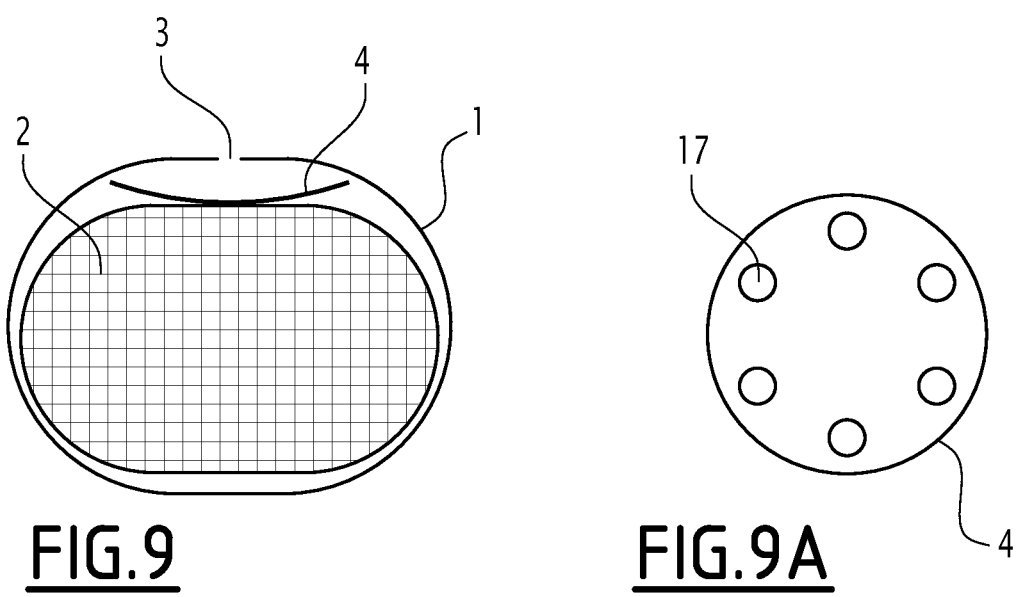
FIG. 9 represents an eighth embodiment of the closing mechanism comprising a flap of dish shape.
FIG. 9A represents a top view of the closing mechanism represented in FIG. 9.

According to an eighth embodiment represented in FIG. 9, the flap 4 has the shape of a concave dish, the circumference whereof is perforated with perforations 17 allowing the intake of intestinal fluid via the opening 3.

The different closing systems 5 to 9 described above may all comprise a film 5, 7, 8 or particles 6, 7, 8 comprising a polymer suitable for forming with the casing channels whereby the intestinal fluid is suitable for circulating and attaining the inner material, facilitating the intake of intestinal fluid inside the device. This film 5, 7, 8 and these particles 6, 7, 8 made of polymer are particularly as defined above in embodiments 2, 3 and 4.

As explained hereinafter, the inner material, by swelling, contributes to the closure of the closing system by applying a force on one of the components thereof. Preferably, the system for closing the opening of the device does not comprise inner material.

The present invention also relates to a method (P1) for collecting a sample of intestinal fluid comprising:
  i) ingestion of at least one device for collecting a sample of intestinal fluid as defined above;
  ii) passage of the at least one device to the intestine, whereby the gastro-resistant material dissolves, which frees the opening(s);
  iii) intake of intestinal fluid into the casing via the opening(s), whereby the inner material swells by absorbing intestinal fluid to a volume greater than or equal to $1.1 \times V_i$;
  iv) closure of the mechanism for closing the opening;
  v) retrieval of the device(s) in stools.

The method (P1) may be applied to humans or animals.

During step ii) of the method (P1), the device passes through the stomach and is found in the presence of gastric fluid. The device is stable in the presence of gastric fluid thanks particularly to the fact that a gastro-resistant material suitable for dissolving in intestinal fluid at 37° C. is disposed on top of each opening, and that the casing is impervious to gastric fluid. This means that the device is not deformed and does not disintegrate in contact with gastric fluid. At the end of step ii) of the method, the device is located in the intestines and is therefore in contact with intestinal fluid, which causes the dissolution of the gastro-resistant material, and renders the opening accessible to intestinal fluid, enabling step iii). During step iii), the opening is at least partially open, preferably it is completely open. The opening is completely open when all the gastro-resistant material blocking the opening has dissolved in contact with intestinal fluid.

During step iii), the intestinal fluid is taken into the casing via the opening, and more particularly into the open cell structure of the inner material which swells, whereby the intestinal fluid is collected.

The open cell structure of the inner material enables free circulation of the intestinal fluid. The absorption of intestinal fluid into the inner material results in the swelling thereof, up to a volume greater than or equal to $1.1 \times V_i$, particularly greater than or equal to $2 \times V_i$, preferably greater than or equal to $6 \times V_i$.

The intake of intestinal fluid into the collection device during step iii) generates a motive swelling force. This swelling force is typically calculated so as to be adapted to the counterforce applied by the casing encasing the inner material due to the elasticity thereof. This makes it possible to define precisely upstream of the method (P1) the parameters in respect of size, shape and volume of the collection device.

The method (P1), and particularly step iii), is therefore based on an equilibrium of forces between the inner material and the casing. Before being ingested, the at least partially compressed inner material remains compressed even if no force opposes same. During step iii), the inner material absorbs the intestinal fluid and swells. During the swelling, the interconnected cells of the cell structure spread out, thus forming a reservoir of intestinal fluid, and above all of microbiota. The intestinal fluid absorbed by the inner material applies a centrifugal swelling force which is continuously compensated by the centripetal counterforce of the casing constraining same. The whole, opposing, on one hand, a swelling pressure reserve of the inner material and, on the other, the stress tension of the casing, provides the driving force that is required for collecting intestinal fluid.

Advantageously, the device is capable of retaining throughout the digestive process the intestinal fluid collected and containing the microbiota to be subsequently analysed. Advantageously, the device makes it possible to keep the microbiota alive.

The gastro-resistant material is generally presented in the form of a layer disposed on top of each opening. Advantageously the time and location of intestinal fluid collection are predetermined by the pH, thickness and/or quantity of the layer of gastro-resistant material disposed on top of the outer surface of the opening, thus determining the duration of the dissolution thereof. Thus, a small thickness of the layer of gastro-resistant material, or a small quantity of this material enables rapid dissolution and therefore rapid collection. Conversely, a large thickness of the layer of gastro-resistant material, or a large quantity, delays the complete dissolution thereof and favours slower collection. The combination of the thickness and/or quantity of the layer of gastro-resistant material with the solubility thereof according to the pH makes it possible to predetermine the exact location of intestinal fluid collection.

Generally, carrying out step iii) of the method (P1) triggers step iv). In other words, the intake of intestinal fluid into the device causes swelling of the inner material which induces the closure of the mechanism for closing the opening(s). Advantageously, step iv) of the method (P1) is triggered when the device is at least partially filled with intestinal fluid. The mechanism for closing the opening(s) is actuated by swelling the inner material in contact with intestinal fluid. Thus, the closure of the closing mechanism is carried out thanks to the equilibrium of the swelling force and the counterforce of the casing.

Preferably, the total duration of steps iii) and iv) is less than 5 min.

The closure of the closing mechanism makes it possible for the sample of intestinal fluid collected not to be subsequently contaminated during the digestive process.

In the first embodiment of the mechanism for closing the orifice 3, during step iii), the inner material 2 swells, then applying a pressure on the flap 4 which is deformed to fit the shape of the casing 1. The more the volume of intestinal fluid taken into the device increases, the more the pressure applied by the inner material 2 onto the flap 4 increases, which strengthens the contact between the flap 4 and the casing 1, making it possible to block the opening 3 effectively. In the particular case where the casing 1 and the flap 4 consist of silicone, the cohesion between the flap 4 and the casing 1 is accentuated by the gummy consistency and the hydrophobic interactions therebetween.

In the first alternative of the second embodiment of the mechanism for closing the opening 3, the film 5 and the casing 1 form together channels whereby the intestinal fluid is suitable for circulating and attaining the inner material, which enables the intake of intestinal fluid into the device. When the intestinal fluid circulates in the channels, the polymeric film 5 dissolves, the channels disappear and the flap 4 sticks to the opening 3, which results in the closure of the opening 3.

In the second alternative of the second embodiment of the mechanism for closing the opening 3, the particles 6 and the casing 1 form together channels whereby the intestinal fluid is suitable for circulating and attaining the inner material, which enables the intake of intestinal fluid into the device. When the intestinal fluid circulates in the channels, the polymeric particles 5 dissolve, the channels disappear and the flap 4 sticks to the opening 3, which results in the closure of the opening 3.

In the third embodiment of the mechanism for closing the opening 3, during step iii) of the method (P1), the polymers of the film and/or the particles 7 and 8 are solubilised in contact with intestinal liquid, and react with one another by means of an esterification reaction. The polyester formed hardens and makes it possible to block the opening 3 effectively. The duration of the esterification is sufficiently long for the collection of intestinal fluid to take place.

In the fourth embodiment of the mechanism for closing the orifice 3, the contacts 9 of the flap 4 keep a space between the casing 1 and the inner material 2 which enables the entry of intestinal fluid, whereby the inner material 1 swells. Thanks to the pressure released thanks to the swelling of the inner material, the flap 4 curves to fit the shape of the casing 1 perfectly, such that the opening 3 is perfectly blocked.

In the fifth embodiment of the mechanism for closing the opening 3, the radiant channels 11 allow the entry of intestinal fluid via the opening 3, while keeping the casing 1 separated from the inner material 2. The pressure released thanks to the swelling of the inner material enables the press stud 10 to be inserted in the opening 3 and hence blocks same non-reversibly, rendering the entire device impervious to intestinal fluid.

In the sixth embodiment of the mechanism for closing the opening 3, the pressure released thanks to the swelling of the inner material makes it possible to curve the flap 4 such that the press stud 12 facing the opening 3 is inserted therein and blocks same.

In the seventh embodiment of the mechanism for closing the opening 3, when the pressure released thanks to the swelling of the inner material increases, the bead 14 rises in the chamber 16 which blocks the opening 3. When the pressure increases further, the bead 14 cannot pass through the opening 3 and thus locks the opening irreversibly.

In the eighth embodiment of the mechanism for closing the opening 3, the combined action of the swelling of the inner material 2 and the stretching of the casing 1, tends to move the edges of the flap 4 apart, therefore flatten the latter, and pushes the flap progressively towards the casing 1 which reverses the concavity thereof. By pressing on the casing 1, the flap 4 covers the opening 3 hermetically.

Advantageously, it is possible to monitor the collection device during steps i) to iv) of the method (P1) thanks to the presence of a ferromagnetic metal wire comprised in the thickness of the casing. This monitoring may be carried out by radiography or sonography.

Advantageously, step v) of the method (P1) is facilitated by the presence of the ferromagnetic metal wire comprised in the thickness of the casing, retrieval being then carried out thanks to a magnet or any other magnetic device.

Following step v), the intestinal liquid collected in the device may be characterised and the microbiota analysed using any technique known to those skilled in the art. Preferably, the cells of the open cell structure of the retrieved device have a mean internal diameter as measured by scanning electron microscopy of 10 μm to 3 mm. Advantageously, the greatest dimension (diameter or height) of the device is dependent on the subject on which the device is used. Thus, following step v), if the device is intended to be used on a small animal such as a rat, the greatest dimension of the device is less than 2 mm. When the device is used on humans, the greatest dimension is generally less than 10 mm, preferably less than 8 mm.

The present invention also relates to the use of the device for collecting intestinal fluid. The collection device may advantageously be used for collecting intestinal fluid at a predetermined time or location.

The invention also relates to a method (P2) for preparing the device comprising the following steps:
a) Providing a polymeric material having a volume $V_0$ greater than Vi,
b) At least partially compressing said polymeric material to attain a volume $V_i$,
c) Encasing said at least partially compressed polymeric material obtained in step b) in a casing,
d) Applying a gastro-resistant material suitable for dissolving in intestinal fluid at 37° C. on the outer surface of each opening,
α) Incorporating a mechanism for closing the opening(s), step α) optionally being carried out before, during or after step c).

The material provided in step a) is a material corresponding to the inner material defined above, except that it has a volume $V_0$ greater than $V_i$, which therefore means that it is less compressed than the inner material of the device, preferably it is not compressed. Preferably, $V_0$ is greater than or equal to $2 \times V_i$, preferably greater than or equal to $4 \times V_i$. Typically, $V_0$ is between $4 \times V_i$ and $6 \times V_i$.

The polymeric material having a volume $V_0$ is generally a commercial material. Mention may be made for example of polyvinyl alcohol material in the form of foam comprised in surgical dressings suitable for use for absorbing blood during surgical procedures.

Typically, step b) is carried out by means of a clamp or a hydraulic press according to the maximum dimension of the device. The pressure applied is of the order of 5 kg/cm². Generally, the at least partially compressed polymeric material obtained at the end of step b) remains at the volume $V_i$ at the end of step b), even when the compression force is no longer applied. It remains in shape.

Typically, step c) is carried out using any means known to those skilled in the art.

Step α) of the method (P2) may be carried out before, during or after step c). Thus, the opening(s) may already be present on the casing during the encasing of the polymeric material; or they may be formed before or after having disposed the casing.

Typically, step d) of the method (P2) is carried out using any means known to those skilled in the art.

EXAMPLE

Preparation of a Device According to the Invention

The work was performed in a clean, sterile and dust-free environment. The device was prepared from a polyvinyl alcohol (PVA) sponge cellular material such as those sometimes used by surgeons to mop up an operation area. A sample of this material having a thickness of 10 mm was placed on a solid surface. Using a punch cutting 10 mm in diameter, a cylinder in the format 10×10 mm was cut out and detached. This cylinder was then compressed using a clamp to obtain a disk of format 10×2 mm. With the same punch, a flap was cut out of a polyethylene film of 0.2 mm thickness that was overlaid on the compressed disk. The whole was placed in a casing composed of a finger of a butadiene-acrylonitrile surgical glove. The glove finger was knotted to form a hermetic casing while identifying the position of the flap inside. Using a fine-tipped clamp, a 1 mm diameter opening was made in the butadiene-acrylonitrile copolymer casing above the centre of the flap without damaging the latter. This device is characterised by dimensions suitable for animal testing on pigs.

The following volumes were measured:

| | |
|---|---|
| Material volume | $V_0 = 0.785$ ml |
| Compressed volume | $V_i = 0.157$ ml |
| Material volume after swelling | $V = 0.470$ ml |
| Collected intestinal fluid volume | $V = 0.310$ ml |

The nitrile casing has a hardness of 50 Shore and a Young modulus of 1.5 MPa. Once compressed, the mean pore diameter of the PVA inner material was between 7 and 12 μm. After collecting intestinal fluid, the mean pore diameter of the inner material was between 80 and 200 μm. The elongation in the wet state was 250%. The porosity was between 89 and 91%. In the dry state, the pore volume was 0.56 cm³ g⁻¹.

The invention claimed is:
1. A device for collecting a sample of intestinal fluid comprising:
a polymeric inner material:
having an at least partially compressed open cell structure, and
having a volume $V_i$,
an elastic polymeric casing impervious to digestive fluid, said casing comprising at least one opening,
a gastro-resistant material suitable for dissolving in intestinal fluid at 37° C. being disposed on top of each of said at least one opening; and
at least one mechanism for closing the at least one opening, an intake of intestinal fluid into the device causing swelling of the inner material which induces a closure of the mechanism for closing the at least one opening,
wherein the polymeric inner material is suitable for swelling to a volume greater than or equal to $1.1 \times V_i$ by absorbing intestinal fluid,
wherein the elastic polymeric casing defines an inner volume where the polymeric inner material is disposed, and the polymeric inner material is configured to, once swollen with the intestinal fluid sample, occupy at least 80% of the inner volume formed by the elastic polymeric casing,
wherein the casing encases the inner material, said at least one opening allowing the intake of intestinal fluid into the inner material, such that swelling of the inner material causes elastic deformation of the casing, and
wherein the mechanism for closing the at least one opening comprises a flap impervious to intestinal fluid, the flap being inserted between the casing and the inner material and disposed under the at least one opening, a first film or first particles disposed between the flap and the casing and comprising a first polymer carrying hydroxyl, carboxylic acid and/or carboxylate functions; and a second film or second particles disposed between the first film or the first particles and the flap and comprising a second polymer carrying hydroxyl, carboxylic acid and/or carboxylate functions;

where the first film or the first particles comprising the first polymer, the second film or the second particles comprising the second polymer and the casing form together channels whereby intestinal fluid is suitable for circulating and attaining the inner material, on condition that:

the first and second polymers are suitable for reacting together to form a polyester during the circulation of intestinal liquid in the channels, when (i) the first polymer carries hydroxyl functions, the second polymer carries carboxylic acid and/or carboxylate functions, or (ii) the first polymer carries carboxylic acid and/or carboxylate functions, the second polymer carries hydroxyl functions.

2. The device according to claim 1, wherein the polymer of the casing is selected from the group consisting of latexes, polyvinyls, nitrile polymers, silicone, and a mixture thereof.

3. The device according to claim 1, wherein the inner material is suitable for swelling to a volume greater than or equal to $2 \times V_i$ by absorbing intestinal fluid.

4. The device according to claim 1, wherein the polymer of the inner material is selected from the group consisting of at least partially cross-linked polyvinyl alcohols, at least partially cross-linked poly(meth)acrylic acids and salts thereof, at least partially cross-linked polysaccharides, and a mixture thereof.

5. The device according to claim 1, wherein the mechanism for closing the at least one opening comprises the first film or the first particles of mean diameter between 0.10 mm and 2 mm, and the second film or the second particles of mean diameter between 0.10 mm and 2 mm, the first and second polymers being suitable for dissolving at 37° C. in intestinal fluid.

6. The device according to claim 1, suitable for collecting a volume of intestinal fluid between 0.01 mL and 1 mL.

7. A method for collecting a sample of intestinal fluid comprising:

i) ingestion of at least one device according to claim 1;

ii) passage of the at least one device to the intestine, whereby the gastro-resistant material dissolves, which frees the at least one opening;

iii) intake of intestinal fluid into the casing via the at least one opening, whereby the inner material swells by absorbing intestinal fluid to a volume greater than or equal to $1.1 \times V_i$;

iv) closure of the mechanism for closing the at least one opening; and v) retrieval of the at least one device in stools.

8. A method for collecting intestinal fluid into a casing from at least one opening to cause swelling of an inner material where the method comprises utilizing the device according to claim 1.

9. The device according to claim 1, wherein the intake of the intestinal fluid into the polymeric inner material applies a pressure into the flap to block the at least one opening, the polymeric inner material, once swollen, being in direct contact with the flap.

10. The device according to claim 1, wherein the elastic polymeric casing has an unstretched configuration and a stretched configuration, an internal space in the unstretched configuration is smaller than an internal space in the stretched configuration, and the elastic polymeric casing is stretchable under a force of 1N at 25° C. over a length between 2 times to 6 times an initial length thereof.

11. A device for collecting a sample of intestinal fluid comprising:

a polymeric inner material:
having an at least partially compressed open cell structure, and
having a volume $V_i$, an elastic polymeric casing impervious to digestive fluid, said casing comprising at least one opening, a gastro-resistant material suitable for dissolving in intestinal fluid at 37° C. being disposed on top of each of said at least one opening; and at least one mechanism for closing the at least one opening, an intake of intestinal fluid into the device causing swelling of the inner material which induces a closure of the mechanism for closing the at least one opening, wherein the inner material is suitable for swelling to a volume greater than or equal to $1.1 \times V_i$ by absorbing intestinal fluid, the casing encases the inner material, said at least one opening allowing the intake of intestinal fluid into the inner material, such that swelling of the inner material causes elastic deformation of the casing, the mechanism for closing the at least one opening comprises a flap impervious to intestinal fluid, the flap being inserted between the casing and the inner material and disposed under the at least one opening;

a first film or first particles disposed between the flap and the casing and comprising a first polymer carrying hydroxyl, carboxylic acid and/or carboxylate functions; and a second film or second particles disposed between the first film or the first particles and the flap and comprising a second polymer carrying hydroxyl, carboxylic acid and/or carboxylate functions;

where the first film or the first particles comprising the first polymer, the second film or the second particles comprising the second polymer and the casing form together channels whereby intestinal fluid is suitable for circulating and attaining the inner material, on condition that:

the first and second polymers are suitable for reacting together to form a polyester during the circulation of intestinal liquid in the channels, when (i) the first polymer carries hydroxyl functions, the second polymer carries carboxylic acid and/or carboxylate functions, or (ii) the first polymer carries carboxylic acid and/or carboxylate functions, the second polymer carries hydroxyl functions.

* * * * *